United States Patent
Lin et al.

(10) Patent No.: US 7,745,155 B2
(45) Date of Patent: Jun. 29, 2010

(54) IN-VIVO MONITORING OF CIRCULATING APOPTOTIC CELLS

(75) Inventors: Charles P. Lin, Arlington, MA (US); Xunbin Wei, Quincy, MA (US); Dorothy Sipkins, Evanston, IL (US)

(73) Assignee: Massachusetts General Hospital, Boston, MA (US)

( * ) Notice: Subject to any disclaimer, the term of this patent is extended or adjusted under 35 U.S.C. 154(b) by 473 days.

(21) Appl. No.: 11/190,729

(22) Filed: Jul. 27, 2005

(65) Prior Publication Data

US 2006/0134005 A1 Jun. 22, 2006

Related U.S. Application Data

(63) Continuation-in-part of application No. 11/015,334, filed on Dec. 17, 2004, now Pat. No. 7,491,502.

(51) Int. Cl.
*G01N 33/574* (2006.01)
*G01N 21/00* (2006.01)
*G01N 21/66* (2006.01)
*A61K 49/00* (2006.01)

(52) U.S. Cl. .......... 435/7.23; 435/7.21; 435/7.24; 435/286.5; 435/287.2; 436/517; 436/546; 436/10; 436/56; 436/63; 436/64; 436/164; 436/172; 424/9.1; 422/73; 422/82.08; 422/82.09

(58) Field of Classification Search .......... 424/9.1, 424/9.6, 9.8; 435/7.21, 7.23, 7.24, 286.5, 435/287.2; 436/517, 546, 63, 64, 148, 172, 436/10, 56, 164; 422/73, 82.05, 82.08, 82.09
See application file for complete search history.

(56) References Cited

U.S. PATENT DOCUMENTS

| 5,644,388 A | 7/1997 | Maekawa et al. |
| 5,976,502 A | 11/1999 | Khoobehi et al. |
| 6,337,920 B1 | 1/2002 | Muhlhoff |

(Continued)

FOREIGN PATENT DOCUMENTS

WO WO-9834536 8/1998

OTHER PUBLICATIONS

Novak et al., In vivo flow cytometer for real-time detection and quantification of circulating cells, Optical Letters, 29 (1): 77-79 (Jan. 1, 2004).*

(Continued)

*Primary Examiner*—Gailene R Gabel
(74) *Attorney, Agent, or Firm*—Nutter McClennen & Fish LLP

(57) ABSTRACT

The present invention provides methods and systems for performing in vivo flow cytometry. In one embodiments, selected circulating cells of interest of a subject are labeled with fluorescent probe molecules. The labeled cells are irradiated in-vivo so as to excite the fluorescent probes, and the radiation emitted by the excited probes is detected, preferably confocally. The detected radiation is then analyzed to derive desired information, such as relative cell count, of the cells of interest. In some embodiments, the circulating cells comprise apoptotic cells whose detection can allow, e.g., non-invasive monitoring of the efficacy of a cancer treatment, such as an anti-tumor or an anti-angiogenic therapy.

11 Claims, 8 Drawing Sheets

U.S. PATENT DOCUMENTS

| | | | |
|---|---|---|---|
| 6,462,345 | B1 | 10/2002 | Simon et al. |
| 6,507,400 | B1 | 1/2003 | Pina et al. |
| 6,548,796 | B1 | 4/2003 | Silvermintz et al. |
| 6,549,275 | B1 | 4/2003 | Cabuz et al. |
| 6,554,775 | B1 | 4/2003 | Peyman et al. |
| 6,589,792 | B1 | 7/2003 | Malachowski |
| 6,597,438 | B1 | 7/2003 | Cabuz et al. |
| 6,646,742 | B1 | 11/2003 | Gangstead et al. |
| 6,687,052 | B1 | 2/2004 | Wilson et al. |
| 6,727,071 | B1 | 4/2004 | Dunlay et al. |
| 6,811,983 | B2 | 11/2004 | Sugden et al. |
| 7,264,794 | B2 | 9/2007 | Georgakoudi et al. |
| 7,491,502 | B2 | 2/2009 | Lin |
| 2005/0101524 | A1 | 5/2005 | Hogg |
| 2006/0134002 | A1 | 6/2006 | Lin |
| 2006/0134005 | A1* | 6/2006 | Lin et al. ............. 424/9.6 |
| 2007/0111225 | A1 | 5/2007 | Lambert et al. |
| 2007/0249734 | A1* | 10/2007 | Gilbert et al. ........... 514/775 |
| 2007/0274919 | A1 | 11/2007 | Dertinger |

OTHER PUBLICATIONS

Georgakoudi et al., In Vivo Flow Cytometer: A New Method for Enumerating Circulating Cancer cells, Cancer Research, 64: 5044-5047 (Aug. 1, 2004).*

Petrovsky et al., Near-Infrared Fluorescent Imaging of Tumor Apoptosis, Cancer Research 63: 1936-1942 (Apr. 15, 2003).*

Yamamoto et al., Granulocytes from patients with paroxysmal nocturnal hemoglobinuria and normal individuals have the same sensitivity to spontaneous apoptosis, Experimental Hematology 30: 187-194 (2002).*

Carbonari et al., Detection and Characterization of Apoptotic Peripheral Blood Lymphocytes in Human Immunodeficiency Virus Infection and Cancer Chemotherapy by a Novel Flow Immunocytometric Method, Blood 83 (5): 1266-1277 (Mar. 1, 1994).*

Database BIOSIS, Accession No. 2005; 535990, Buller G. Monomeric Cyanine dye permeability correlated with annexin-V staining on apoptotic cells using flow cytometry. FASEB Journal, Mar. 7, 2005, vol. 19, No. 5, Suppl. S, Part 2, pp. A1673 Abstract.

Database BIOSIS, Accession No. 2002: 2780, Nicholas, A.P. In vitro neuronal cell death mediated by alpha-1 A/D adrenoceptors. Society of Neuroscience Abstracts. 2001, vol. 27, No. 2, pp. 2141. Abstract.

Aotake, T., et al., "Changes of angiogenesis and tumor cell apoptosis during colorectal carcinogenesis", 1999, Clin Cancer Res 5(1):135-142.

Bedner, E., et al., "High affinity binding of fluorescein isothiocyanate to esosinophils detected by laser scanning cytometry: a potential source of error in analysis of blood samples utilizing fluorescein-conjugated reagents in flow cytometry", 1999, Cytometry 36(1):77-82.

Blankenberg, F.G., et al., "Imaging cyclophosphamide-induced intramedullary apoptosis in rats using 99mTc-cradiolabeled annexin", 2001, Journal of Nuclear Medicine 42(2):309-316.

Brooks, P.C., et al., "Integrin alpha v beta 3 antagonists promote tumor regression by inducing apoptosis of angiogenic blood vessels", 1994, Cell 79(7):1157-1164.

Carbonari, M., et al., "Detection and characterization of apoptotic peripheral blood lymphocytes in human immunodeficiency virus infection and cancer chemotherapy by a novel flow immunocytometric method", 1994, Blood 83(5):1268-1277.

Cummings, M.C., "Apoptosis", 1997, Am J Surg Pathol 21(1):88-101.

Durrieu, F., et al., "Caspase activation is an early event in anthracycline-induced apoptosis and allows detection of apoptotic cells before they are ingested by phagocytes", 1998a, Exp Cell Res 240(2):165-175.

Ek, O., et al., "Treatment of human B-cell precursor leukemia in SCID mice by using a combination of the anti-CD19 immunotoxin B43-PAP with the standard chemotherapeutic drugs vincristine, methylprednisolone, and L-asparaginase", 1998a, Leuk Lymphoma 31(1-2):143-149.

Ek, O., et al., "Combined therapeutic efficacy of the thymidylate synthase inhibitor ZD1694 Tomudex) and the immunotoxin B43(anti-CD19)-PAP in a SCID mouse model of human B-lineage acute lymphoblastic leukemia", 1998b, Leuk Lymphoma 28(5-6):509-514.

Fadeel, B., "Apoptosis in human disease: a new skin for the old ceremony?", 1999, Biochem Biophys Res Commun 266(3):699-717.

Gaiano, N., "A method for rapid gain-of function studies in the mouse embryonic nervous system", 1999, Nat Neurosci 2(9):812-819.

Gaiano, N., "Radial glial identity is promoted by Notch1 signaling in the murine forebrain", 2000, Neuron 26(2):395-404.

Georgakoudi, I., "in vivo flow cytometry: a new method of enumerating circulating cancer cells", 2004, Cancer Res 64(15);5044-5047.

Herschman, H.R., "Molecular imaging: looking at problems, seeing solutions", 2003, Science 302(5645):605-608, Holdenrieder, S., "Apoptotic markers in cancer", 2004, Clin Biochem 37(7):605-617.

Jarh, S., "DNA fragments in the blood plasma of cancer patients: quantitations and evidence for their origin from apoptotic and necrotic cells", 2001, Cancer Res 61(4):1659-1665.

Johnston, J.B., et al., "Induction of apoptosis in CD4+ prolymphocytic leukemia by deoxyadenosine and 2'-deoxycoformycin", 1992, Leukemia Research 16(8):781-788.

Laxman, B., "Noninvasive real-time imaging of apoptosis", 2002, Proceedings of the National Academy of Sciences of the United States of America 99(26):16551-16555.

Massoud, T.F., et al., "Molecular imaging in living subjects: seeing fundamental biological processes in a new light", 2003, Genes & Development, 17(5):545-580.

Matsubara, K, et al., "Induction of apoptosis in childhood acute leukemia by chemotherapeutic agents: failure to detect evidence of apoptosis in vivo", 1994, European Journal of Haematology 52(1):47-52.

Nery, S., et al., "Sonic hedgehog contributes to oligodendrocyte specification in the mammalian forebrain", 2001, Development 128(4):527-540.

Novak, J., et al., "In vivo flow cytometer for real-time detection and quantification of circulating cells", 2004, Opt Lett 29(1):77-79.

Ntziachristos, V., et al., "Visualization of antitumor treatment by means of fluorescence molecular tomography with an annexin V-Cy5.5 conjugate", 2004, Proc Natl Acad Sci USA 101(33):12294-12299.

Osella-Abate, S., et al., "Expression of apoptosis markers on peripheral blood lymphocytes from patients with cutaneous T-cell lymphoma during extracorporeal photochemotherapy", 2001, J Am Acad Dermatol 44(1):40-47.

Petrovsky, A., et al, "Near-infrared fluorescent imaging of tumor apoptosis", 2003, Cancer Research 63(8):1936-1942.

Reed, J., "Dysregulation of apoptosis in cancer", 1999, J Clin Oncol 17(9):2941-2953.

Rich, T., et al., "Defying death after DNA damage", 2000, Nature 407(6805):777-783.

Saito, T., et al., "Spontaneous ex vivo apoptosis of peripheral blood mononuclear cells in patients with head and neck cancer", 1999, Clinical Cancer Research 5(6):1263-1273.

Savill, J., et al., "Corpse clearance defines the meaning of cell death", 2000, Nature 407(6805):784-788.

Schellenberger, E.A., et al., "Optical imaging of apoptosis as a biomarker of tumor response to chemotherapy", 2003, Neoplasia (New York) 5(3):187-192.

Solovey, A., et al., "Sickle cell vascular endothelial growth factor on circulating and unanchored endothelial cells", 1999, Blood 93(11):3824-3830.

Stroun, M., et al., "The origin and mechanism of circulating DNA", 2000, Ann N Y Acad Sci 906:161-168.

Sulowska, Z., et al., "Effect of exogenous opioid peptides on TNF-alpha-induced human neutrophil apoptosis in vitro", 2003, Archivum Immunologiae et Therapiae Experimentalis 51(4):267-272.

Thompson, C.B., "Apoptosis in the pathogenesis and treatment of disease", 1995, Science 267(5203):1456-1462.

Uckun, F.M., et al., "Effective immunochemotherapy of CALLA+C mu+ human pre-B acute lymphoblastic leukemia in mice with severe combined immunodeficiency using B43 (anti-CD19)-pokeweed antiviral protein immunotoxin plus cylophosphamide", 1992a, *Blood* 79(12):3116-3129.

Uckun; F.M., et al., "In vivo efficacy of B43 (anti-CD19)-pokeweed antiviral protein immunotoxin against human pre-B cell acute lymphoblastic leukemia in mice with severe combined immunodeficiency", 1992b, *Blood* 79(9):2201-2214.

Weber, W.A., et al., "Tumor angiogensis targeting using imaging agents", 2001, Quarterly Journal of Nuclear Medicine 45(2):179-182.

Alt, Clemens, "Advances in in vivo flow cytometry," Tufts University, Biomedical Engineering Department Fall 2005 Seminar Series, XP002493305, Nov. 6, 2006.

Backman V, Gopal V, Kalashnikov M, et al. Measuring cellular structure at submicron scale with light scattering spectroscopy. IEEE J Sel Top Quantum Electron 2001; 7: 887-93.

Backman V, Gurjar R, Badizadegan K, et al. Polarized light scattering spectroscopy for quantitative measurement of epithelial cellular structures. IEEE J Sel Top Quantum Electron 1999; 5: 1019-26.

Bassan R, Gatta G, Tondini C, Willemze R. Adult acute lymphoblastic leukeamia. Crit Rev Onc Hematol 2004; 50: 223-61.

Bigio I, Bown S, Briggs G, et al. Diagnosis of breast cancer using elastic-scattering spectroscopy: preliminary clinical results. J Biomed Opt 2000; 5: 221-8.

Bolay H, Reuter U, Dunn AK, Huang Z, Boas DA, Moskowitz MA. Intrinsic brain activity triggers trigeminal meningeal afferents in a migraine model. Nat Med 2002; 8: 136-42.

Borenstein J, Terai H, King K, Weinberg E, Kaazempur-Mofrad M, Vacanti J. Microfabrication technology for vascularized tissue engineering. Biomedical Microdevices 2002; 4:3: 167-75.

Brisco MJ, Condon J, Hughes E, et al. Outcome prediction in childhood acute lymphoblastic leukaemia by molecular quantification of residual disease at the end of induction. Lancet 1994; 343: 196-200.

Calvi LM, Adams GB, Weibrecht KW, et al. Osteoblastic cells regulate the haematopoietic stem cell niche. Nature 2003; 425: 841-6.

Cave H, van der Werff ten Bosch J, Suciu S, et al. Clinical significance of minimal residual disease in childhood acute lymphoblastic leukemia, European Organization for Research and Treatment of Cancer—Childhood Leukemia Cooperative Group. N. EnglJ Med 1998; 339: 591-8.

Cheng T, Rodrigues N, Shen H, et al. Hematopoietic stem cell quiescence maintained by p21cip1/waf1. Science 2000; 287: 1804-8.

Communication from the International Search Authority, Invitation to Pay Additional Fees with Partial International Search Report, PCT Form ISA/206.

Communication from the International Search Authority, International Search Report and Written Opinion, PCT/US2008/062438, Mar. 12, 2008, 18 pages.

Coustan-Smith E, Behm FG, Sanchez J, et al. Immunological detection of minimal residual disease in children with acute lymphoblastic leukaemia. Lancet 1998; 351: 550-4.

Coustan-Smith E, Sancho J, Hancock ML, et al. Clinical importance of minimal residual disease in childhood acute lymphoblastic leukemia. Blood 2000; 96: 2691-6.

Coustan-Smith E, Sancho J, Hancock ML, et al. Use of peripheral blood instead of bone marrow to monitor residual disease in children with acute lymphoblastic leukemia. Blood 2002; 100: 2399-402.

de Grooth B, Terstappen L, Pupples G, Greve J. Light-scattering polarization measurements as a new parameter in flow cytometry. Cytometry 1987; 8: 539-44.

Dodd SJ, Williams M, Suhan JP, Williams DS, Koretsky AP, Ho C. Detection of single mammalian cells by high-resolution magnetic resonance imaging. Biophys J 1999; 76: 103-9.

Dubey P, Su H, Adonai N, et al. Quantitative imaging of the T cell antitumor response by positron-emission tomography. Proc Natl Acad Sci U S A 2003; 100: 1232-7.

Dunn AK, Bolay H, Moskowitz MA, Boas DA. Dynamic imaging of cerebral blood flow using laser speckle. J Cereb Blood Flow Metab 2001; 21: 195-201.

Dunn AK, Devor A, Bolay H, et al. Simultaneous imaging of total cerebral hemoglobin concentration, oxygenation, and blood flow during functional activation. Opt Lett 2003; 28: 28-30.

Facts and Figures. National Institute of Allergy and Infectious Diseases, Aug. 2005.

Fidler I. Metastasis: quantitative analysis of distribution and fate of tumor emboli-labeled with .sup.T251-5-Iodo-2'-deoxyuridine. J Nat/ Cancer Inst 1970; 45: 773-82.

Fidler I. The pathogenesis of cancer metastasis: the 'seed and soil' hypothesis revisited. Nature Rev Cancer 2003; 3: 453-8.

Ford AM, Fasching K, Panzer-Grumayer ER, Koenig M, Haas OA, Greaves MF. Origins of "late" relapse in childhood acute lymphoblastic leukemia with TEL-AML1 fusion genes. Blood 2001; 98: 558-64.

Fournier M, Gireau A, Chretien MC, et al. Laboratory evaluation of the Abbott Cell DYN 3500 5-part differential. Am J Clin Pathol 1996; 105: 286-92.

Georgakoudi I, Jacobson B, Van Dam J, et al. Fluorescence, reflectance and light scattering spectroscopy for evaluating dysplasia in patients with Barrett's esophagus. Gastroenterol 2001; 120: 1620-9.

Georgakoudi I, Sheets EE, Muller MG, et al. Tri-Modal Spectroscopy for the detection and characterization of cervical pre-cancers in vivo. Am J Obstet Gynecol 2002; 186: 374-82.

Gurjar RS, Backman V, Perelman LT, et al. Imaging human epithelial properties with polarized light-scattering spectroscopy. Nat Med 2001; 7: 1245-8.

Janossy G, Bollum FJ, Bradstock KF, Ashley J. Cellular phenotypes of normal and leukemic hemopoietic cells determined by analysis with selected antibody combinations. Blood 1980; 56: 430-41.

Kaihara S, Borenstein J, Koka R ea. Silicon micromachining to tissue engineer branched vascular channels for liver fabrication. Tissue Eng 2000; 6: 105-17.

Kiger AA, White-Cooper H, Fuller MT. Somatic support cells restrict germline stem cell self-renewal and promote differentiation. Nature 2000; 407: 750-4.

Knechtli CJ, Goulden NJ, Hancock JP, et al. Minimal residual disease status before allogeneic bone marrow transplantation is an important determinant of successful outcome for children and adolescents with acute lymphoblastic leukemia. Blood 1998;92: 4072-9.

Konrad M, Metzler M, Panzer S, et al. Late relapses evolve from slow-responding subclones in t(12;21)-positive acute lymphoblastic leukemia: evidence for the persistence of a preleukemic clone. Blood 2003; 101: 3635-40.

Krauter J, Wattjes MP, Nagel S, et al. Real-time RT-PCR for the detection and quantification of AML1/MTG8 fusion transcripts in t(8;21)-positive AML patients. Br J Haematol 1999; 107: 80-5.

Lein M, Koenig F, Misdraji J, et al. Laser-induced hyperthermia in rat prostate cancera; role of site of tumor implantation. Urology 2000; 56: 167-72.

Momma T, Hamblin MR, Wu HC, Hasan T. Photodynamic therapy of orthotopic prostate cancer with benzoporphyrin derivative: local control and distant metastasis. Cancer Res 1998; 58: 5425-31.

Mourant JR, Bigio I, Boyer J, Conn R, Johnson TM, Shimada T. Spectroscopic diagnosis of bladder cancer with elastic scattering spectroscopy. Lasers Surg Med 1995; 17: 350-7.

Mourant JR, Bigio I, Boyer J, Johnson TM, Lacey J. Elastic scattering spectroscopy as a diagnostic for differentiating pathologies in the gastrointestinal tract: preliminary testing. J Biomed Opt 1996; 1: 1-8.

Mourant JR, Canpolat M, Brocker C, et al. Light scattering from cells: the contribution of the nucleus and the effects of proliferative status. J Biomed Opt 2000; 5: 131-7.

Mourant JR, Freyer JP, Hielscher AH, Eick AA, Shen D, Johnson TM. Mechanisms of light scattering from biological cells relevant to noninvasive optical-tissue diagnostics. Appl Opt 1998; 37: 3586-93.

Mourant JR, Johnson TM, Carpenter S, Guerra A, Aida T, Freyer JP. Polarized angular dependent spectroscopy of epithelial cells and epithelial cell nuclei to determine the size scale of scattering structures. J Biomed Opt 2002; 7: 378-87.

Muller MG, Valdez T, Georgakoudi I, et al. Spectroscopic detection and evaluation of morphologic and biochemical changes in early human oral carcinoma. Cancer 2003; 97: 1681-92.

Muller MG, Wax A, Georgakoudi I, Dasari R, Feld MS. A reflectance spectrofluorimeter for real-time spectral diagnosis of disease. Rev Sci Instrum 2002; 73: 3933-7.

Myakov A, Nieman L, Wicky L. Utzinger U, Richards-Kortum R, Sokolov K. Fiber optic probe for polarized reflectance spectroscopy in vivo: Design and performance. J Biomed Opt 2002; 7: 388-97.

Naumov GN, Wilson SM, MacDonald IC, et al. Cellular expression of green fluorescent protein, coupled with high-resolution in vivo videomicroscopy, to monitor steps in tumor metastasis. J Cell Sci 1999; 112: 1835-42.

Nyvold C, Madsen HO, Ryder LP, et al. Precise quantification of minimal residual disease at day 29 allows identification of children with acute lymphoblastic leukemia and an excellent outcome. Blood 2002; 99: 1253-8.

Otten G, Loken M. Two color light scattering identifies physical differences between lymphocyte subpopulations. Cytometry 1982; 3: 182-7.

Ost V, Neukammer J, Rinneberg H. Flow cytometric differentiation of erythrocytes and leukocytes in dilute whole blood by light scattering. Cytometry 1998; 32: 191-7.

Padera TP, Kadambi A, di Tomaso E, et al. Lymphatic metastasis in the absence of functional intratumor lymphatics. Science 2002; 296: 1883-6.

Perelman L, Backman V, Wallace M, et al. Observation of periodic fine structure in reflectance from biological tissue: A new technique for measuring nuclear size distribution. Phys Rev Let 1998; 80:627-30.

Potter MN, Steward CG, Oakhill A. The significance of detection of minimal residual disease in childhood acute lymphoblastic leukaemia. Br J. Haematol 1993; 83: 412-8.

Racila E, Euhus D, Weiss AJ, et al. Detection and characterization of carcinoma cells in the blood. Proc Natl Acad Sci U S A 1998; 95: 4589-94.

San Miguel JF, Martinez A, Macedo A, et al. Immunophenotyping investigation of minimal residual disease is a useful approach for predicting relapse in acute myeloid leukemia patients. Blood 1997; 90: 2465-70.

Siddiqua A, Chendil D, Rowland R, et al. Increased expression of PSA mRNA during brachytherapy in peripheral blood of patients with prostate cancer. Urology 2002; 60: 270-5.

Smith M, Arthur D, Camitta B, et al. Uniform approach to risk classification and treatment assignment for children with acute lymphoblastic leukemia. J Clin Oncol 1996; 14: 18-24.

Sokolov K, Drezek R, Gossage K, Richards-Kortum R. Reflectance spectroscopy with polarized light: is it sensitive to cellular and nuclear morphology? Opt Express 1999; 5: 302-17.

Spradling A, Drummond-Barbosa D, Kai T. Stem cells find their niche. Nature 2001; 414: 98-104.

Streekstra G, Hoekstra A, Nijhof E-J, Heethaar R. Light scattering by red blood cells in ektacytometry:Fraunhofer versus anomalous diffraction. Appl Opt 1993; 32: 2266-72.

Surveillance, Epidemiology and End Results (SEER) Program. National Cancer Institute, 1975-2000.

Sweeney TJ, Mailander V, Tucker AA, et al. Visualizing the kinetics of tumor-cell clearance in living animals. Proc Natl Acad Sci U S A 1999; 96: 12044-9.

Terstappen L, de Grooth B, ten Napel C, van Berkel W, Greve J. Discrimination of human cytotoxic lymphocytes from regulatory and B-lymphocytes by orthogonal light scattering. J Immunol Methods 1986; 95: 211-6.

Terstappen L, deGrooth B, Visscher K, van Kouterik F, Greve J. Four-parameter white blood cell differential counting based on light scattering measurements. Cytometry 1988; 9: 39-43.

Venditti A, Buccisano F, Del Poeta G, et al. Level of minimal residual disease after consolidation therapy predicts outcome in acute myeloid leukemia. Blood 2000; 96: 3948-52.

Wang JH, Doyle M, Manning BJ, et al. Cutting edge: bacterial lipoprotein induces endotoxin-independent tolerance to septic shock. J Immunol 2003; 170: 14-8.

Wang W, Wyckoff JB, Frohlich VC, et al. Single cell behavior in metastatic primary mammary tumors correlated with gene expression patterns revealed by molecular profiling. Cancer Res 2002; 62: 6278-88.

Wulf G, Luo K, Goodell M, Brenner M. Anti-CD45-mediated cytoreduction to facilitate allogeneic stem cell tranplantation. Blood 2003; 101: 2434-39.

Groner et al., "Orthogonal polarization spectral imaging: a new method for study of the microcirculation," *Nat Med*, 5(10):1209-12 (Oct. 1999).

International Search Report (PCT/US2009/038567) dated Oct. 22, 2009.

Michelson, A. et al.,. Evaluation of platelet function by flow cytometry, Methods vol. 21, pp. 259-270, 2000.

Rajadhyaksha et al., "Video-rate confocal scanning laser microscope for imaging human tissues in vivo," *Appl Optics*, 38(10): 2105-2115 (1999).

* cited by examiner

TIME POST RED BLOOD CELL INJECTION (DAYS)

TIME POST ANTIBODY INJECTION (h)

US 7,745,155 B2

IN-VIVO MONITORING OF CIRCULATING APOPTOTIC CELLS

This application is a continuation-in-part of application Ser. No. 11/015,334 filed Dec. 17, 2004, now U.S. Pat. No. 7,491,502.

RELATED APPLICATION

The present application is a continuation-in-part of application Ser. No. 11/015334 entitled "In Vivo Flow Cytometry System and Method," filed on Dec. 17, 2004, and herein incorporated by reference in its entirety.

GOVERNMENT RIGHTS

The U.S. Government has certain rights in this invention pursuant to grant Nos. NIH EY 14106 and EB 00064 awarded by National Institute of Health (NIH).

BACKGROUND OF THE INVENTION

The present invention relates generally to methods and apparatus for performing flow cytometry, and more particularly, it is directed to such methods and apparatus for conducting real-time in vivo quantification of the flow characteristics of a subject's circulating cells.

Current methods for detecting and quantifying various types of cells circulating within a subject's blood stream typically involve extraction of blood from the subject (a patient or an animal) followed by labeling and ex vivo detection. For example, in standard flow cytometry, specific cell populations in a blood sample, drawn from a subject and fluorescently labeled, are passed in single file through a flow stream to be interrogated by a light source (usually a laser). Fluorescence and light scattering signals emitted, or remitted, by the cells in response to the light source can be employed to determine the types and the number of the cells. In another ex vivo conventional technique, known as hemocytometry, cells are counted against a grid while being viewed with a microscope to determine the types of the cells and their numbers.

Such ex vivo techniques, however, suffer from a number of shortcomings. For example, each measurement provides only a single time sample. Consequently, it is difficult to use these techniques to obtain a valid temporal population profile for a cell type of interest that varies unpredictably or rapidly with time, Further, these techniques can suffer from a significant time delay between sample collection and analysis, leading to potential measurement inaccuracies.

Some in vivo techniques for detection of static and circulating fluorescently labeled cells are also known. However, these techniques typically show difficulty, or simply fail, in tracking cells flowing at a high velocity, especially in the arterial circulation, even when they capture images at video rates. In addition, employing these techniques for extracting quantitative information about the number and flow characteristics of a specific cell population can be very tedious.

In addition, conventional techniques for detecting and monitoring tumor progression and its response to available treatment modalities suffer from similar shortcomings. Methods such as histopathology and standard flow cytometry require taking tissue biopsies or blood samples from the patient. Further, some conventional non-invasive techniques, such as computed tomography, magnetic resonance imaging, and ultrasound, can typically detect only late-stage anatomical abnormalities.

Hence, there is a need for enhanced methods and apparatus for performing in vivo flow cytometry.

There is also a need for such methods and apparatus for non-invasive in-vivo detection of dying/dead cells circulating within a subject, e.g., in order to monitor early response to therapy.

SUMMARY OF THE INVENTION

In one aspect, the present invention provides a method for performing in vivo cytometry by labeling one or more cells of a subject, which are of a selected type, with one or more fluorescent probe molecules while the cells circulate in the subject. The labeled cells are illuminated in vivo with radiation having one or more wavelengths suitable for exciting the fluorescent probe molecules, and fluorescence radiation emitted by the excited probes is detected. The detected fluorescence radiation is then analyzed so as to derive information regarding circulating cells of the selected type.

In a related aspect, the circulating cells can be labeled by introducing the probe molecules into the subject's circulatory system. The probe molecules can, for example, couple to one or more cell surface molecules of the selected cells, such as particular cell membrane proteins. By way of example, a fluorescent probe can be a fluorescently labeled antibody capable of binding to a surface antigen of a cell type of interest. In some embodiments, the cells of interest can be extracted from a subject, labeled ex vivo, and re-introduced into the subject. In some other embodiments, fluorescent proteins can be expressed in vivo in a selected cell type of the subject by utilizing known techniques. For example, transgenic mice having fluorescent proteins in a selected cell type can be designed.

A variety of different cell types can be labeled with such fluorescent probes. Some examples of such cell types, without limitation, include white blood cells, such as leukocytes (lymphocytes, monocytes, granulocytes), tumor cells, such as, leukemic cells, prostate cancer cells and breast cancer cells, and stem cells. Some examples of suitable fluorescent probe molecules include, without limitation, Cy5, Cy5.5, Cy7 AlexaFluor series of probes, and quantum dots.

In another aspect, the information derived from analyzing the fluorescence radiation can provide, for example, a cell count of the circulating cells of a selected type relative to a corresponding count, which was measured previously by employing methods according to teachings of the invention or otherwise. Such a relative cell count can be utilized in a variety of diagnostic and/or treatment protocols as an indicator of presence and/or progression of a disease or efficacy of a treatment regimen. For example, the relative cell count of cancer cells can be indicative of the progress of an applied therapy. In some cases, the fluorescence radiation can be employed to obtain an absolute cell count of a cell type of interest if the diameter of an illuminated vessel and the velocity of blood flow through that vessel can be determined, as discussed in more detail below.

In another aspect, the fluorescence radiation can be analyzed to obtain information about the flow velocity of circulating cells of the selected type. For example, the breadth of fluorescence signal peaks (i.e., a measure of the width of such peaks, such as, full width at half maximum) corresponding to radiation emitted by excited labeled cells can be evaluated to extract such flow velocity information.

A variety of radiation sources and radiation wavelengths can be employed to excite the labeled cells. In general, excitation wavelengths are selected based on the properties of the probe molecules (e.g., wavelengths suitable for exciting these molecules) and the degree of penetrability of such wavelengths into a subject's tissue and blood. By way of example, excitation wavelengths in a range of about 400 nm to about 1000 nm, and more preferably in a range of about 400 nm to about 800 nm, can be utilized. Further, radiation sources can be, e.g., continuous wave (CW) sources. For example, lasers generating radiation having suitable wavelengths can be employed for exciting the labeled cells.

In further aspects of the invention, the fluorescence detection is performed confocally relative to the excitation. As discussed in more detail below, such confocality allows detecting fluorescence from a selected excitation volume while minimizing interference from radiation emanating from regions outside that excitation volume.

In other aspects, the invention provides a method for real-time quantification of circulating cells in a live subject by administering to the subject a plurality of fluorescent probe molecules capable of binding to circulating cells of a selected type, and illuminating at least a portion of a blood vessel (artery or vein) of the subject with radiation that is capable of exciting the fluorescent probe molecules flowing through that vessel portion. Fluorescence radiation originating from one or more of the excited probe molecules is confocally detected, and analyzed to identify fluorescence signals emitted by the probe molecules coupled to the circulating cells. The identified fluorescence signals can be further evaluated to derive information, such as, cell count and/or flow velocity, regarding the selected cell type.

Administration of the probe molecules can be achieved, for example, by injecting a solution containing the probes into a subject's circulatory system. Alternatively, the probe molecules can be orally administered to the subject.

In another aspect, the present invention provides a method of performing in vivo flow cytometry by labeling ex vivo a plurality of cells of a selected type extracted from a subject with fluorescent probe molecules of a type capable of coupling to the cells. The labeled cells can then be introduced into the subject's circulatory system, and illuminated in vivo with radiation having one or more wavelengths suitable for exciting the fluorescent probe molecules. The fluorescence radiation emitted by the excited probe molecules can then detected, and analyzed so as to derive information regarding circulating cells of the selected type, such as cell count and/or flow velocity.

In a related aspect, the fluorescence detection is preferably performed confocally relative to the excitation of the probe molecules.

In another aspect, the invention provides a method of performing in vivo flow cytometry, comprising that includes the steps of expressing a fluorescent protein in a cell type of a subject, illuminating in vivo one or more cells of the cell type with radiation having one or more wavelengths suitable for exciting the fluorescent protein, and detecting fluorescence radiation emitted by the fluorescent protein of the illuminated cells in response to the excitation. The detected fluorescence can then be analyzed so as to derive information regarding circulating cells of that type.

In other aspects, the invention provides a system for performing in vivo cytometry in a live subject that includes a source for generating radiation having one or more wavelength components suitable for exciting selected fluorescent probe molecules that are capable of binding to circulating cells of a selected type of the subject upon introduction into the subject's circulatory system. An optical system images radiation received from the source onto a focal plane in which a portion of a vessel of the subject can be positioned so as to be illuminated by the imaged radiation. The illuminating radiation excites one or more of the molecules flowing through the vessel portion. The system further includes a detector for confocally detecting fluorescence radiation emitted by the excited probe molecules, and an analysis module coupled to the detector for analyzing the fluorescence radiation so as to derive information regarding the circulating cells.

In a related aspect, the cytometry system described above further includes a first spatial filter (e.g., a pinhole or a slit) optically coupled to the radiation source to direct excitation radiation from the source to the optical system that images the radiation onto the labeled cells, and a second spatial filter optically coupled to the detector and positioned so as to be conjugated with respect to the first spatial filter. The optical system focuses the fluorescence radiation onto the second spatial filter, and a detector optically coupled to the second spatial filter detects the radiation. The first and second spatial filters can be, for example, in the form of adjustable-sized slits that can be adjusted to vary the degree of confocality.

In a related aspect, a cylindrical lens is disposed between the radiation source and the first pinhole to modify the cross-sectional shape of a radiation beam received from the source to one having an elongated shape characterized by substantially perpendicular long and short axes. In such a case, the first spatial filter can be in the form of a slit having a height that is larger than its width is substantially aligned with the long axis of the radiation beam's oblong cross-section. The slit can be configured to allow the radiation beam passing therethrough to illuminate a vessel portion such that the beam's long axis substantially traverses a width of the vessel portion.

In a related aspect, a cytometry system according to the teachings of the invention, such as that described above, can include a dichroic beam splitter optically coupled to the radiation source and a fluorescence detector, so as to direct radiation generated by the source towards a vessel of interest and direct fluorescence radiation, emitted by excited labeled cells flowing through the illuminated vessel portion, towards the detector.

In another aspect, the cytometry system can include an analysis module that receives fluorescence data from a detector, and operates on this data to derive information regarding selected flow characteristics of a circulating cell type of interest. The analysis module can include, for example, a filter for substantially removing high frequency noise from the signals generated by the detector, an amplifier for amplifying the filtered signals, and a digitizer (e.g., an analog-to-digital converter (ADC)) for digitizing the filtered amplified signals. A digital signal processing unit (DSP) can provide digital filtering of the digitized signals, and a computing module having the requisite hardware and software components can operate on the digitized signals in accordance with the teachings of the invention to derive selected cytometric information.

In an alternative embodiment, the analysis module can include a photon-counting unit that can convert photoelectric pulses, corresponding to potential fluorescence peaks, generated by the detector into logic pulses and a pulse counter that can count these pulses. A DSP can be optionally utilized to operate on the output of the pulse counter for signal-to-noise enhancement and peak identification. A computing module can operate on the identified peaks in accordance with the teachings of the invention to derive selected cytometric information. In addition, the computing module can include facilities for storage of the fluorescent data and the software for analyzing that data.

In further aspects, the cytometry system can further include an optical system for identifying a vessel portion on which cytometry measurements in accordance with the teachings of the invention can be performed. By way of example, such an optical system can include a radiation source for transilluminating a selected tissue portion of a subject, and an imager, such as a CCD camera, that receives at least a portion of the radiation transmitted through the illuminated tissue to form an image within which a vessel of interest can be identified.

In yet a further aspect, the invention provides a method for non-invasive in-vivo detection of dying or dead cells, herein collectively referred to as non-viable cells (e.g., apoptotic cells such as endothelial apoptotic cells), in a subject. The method can include labeling a plurality of non-viable cells circulating in the subject with cell markers having at least one fluorescent component. The labeled cells are illuminated in-vivo with radiation having one or more wavelength components suitable for exciting the fluorescent component, and fluorescence radiation emitted by the labeled cells in response to this excitation is detected. This is followed by analyzing the detected fluorescence so as to derive information regarding the circulating dying/dead cells. Such information can include, for example, the relative count of those cells.

In a related aspect, the excitation of the labeled cells is achieved by utilizing a radiation source having one or more wavelength components in a range of about 400 nm to about 1000 nm, and the fluorescence radiation is detected confocally relative to the excitation radiation.

In further aspects, in the above method for in-vivo detection of circulating dying/dead cells, the fluorescent marker can be selected to comprise a molecular portion suitable for coupling to a cell surface marker (e.g., a protein or a lipid component) of the dying/dead cells that is conjugated to a fluorescence probe portion. For example, in some embodiments, the fluorescent marker can include a cell marker commonly known as annexin-V conjugated to a fluorescent probe commonly identified as Alexa Fluor 647 (AF647).

In another aspect, a method for non-invasive monitoring of efficacy of a cancer treatment administered to a patient is disclosed. The method includes administering to the subject a plurality of fluorescent cell markers that are capable of labeling a plurality of apoptotic cancer cells circulating in the subject blood. At least a portion of the subject's circulating blood is then illuminated by radiation suitable for exciting the fluorescent markers, and fluorescence radiation emitted by the excited cell markers is detected. The detected fluorescence is then analyzed to derive a relative count of the apoptotic cells. This relative cell count can be, in turn, employed to monitor the progress of a cancer treatment, such as an anti-tumor or an anti-angiogenic therapy.

In a further aspect, the invention provides a method for real-time quantification of dying or dead circulating cells (non-viable circulating cells) in a live subject by administering to the subject a plurality of probe molecules that are capable of coupling to a plurality of circulating non-viable cells. At least a portion of a blood vessel of the subject is illuminated with radiation capable of exciting the fluorescent probe molecules flowing through that vessel portion. The fluorescent radiation originating from one or more of the excited probe molecules is confocally detected, and analyzed to identify fluorescent signals emitted by those excited probe molecules that are coupled to the non-viable circulating cells. The analysis of the emitted fluorescence radiation can further include determining a relative count of the circulating non-viable cells.

Further understanding of the invention can be obtained by reference to the following detailed description in conjunction with the associated drawings, which are described briefly below.

DETAILED DESCRIPTION

Figure 1:
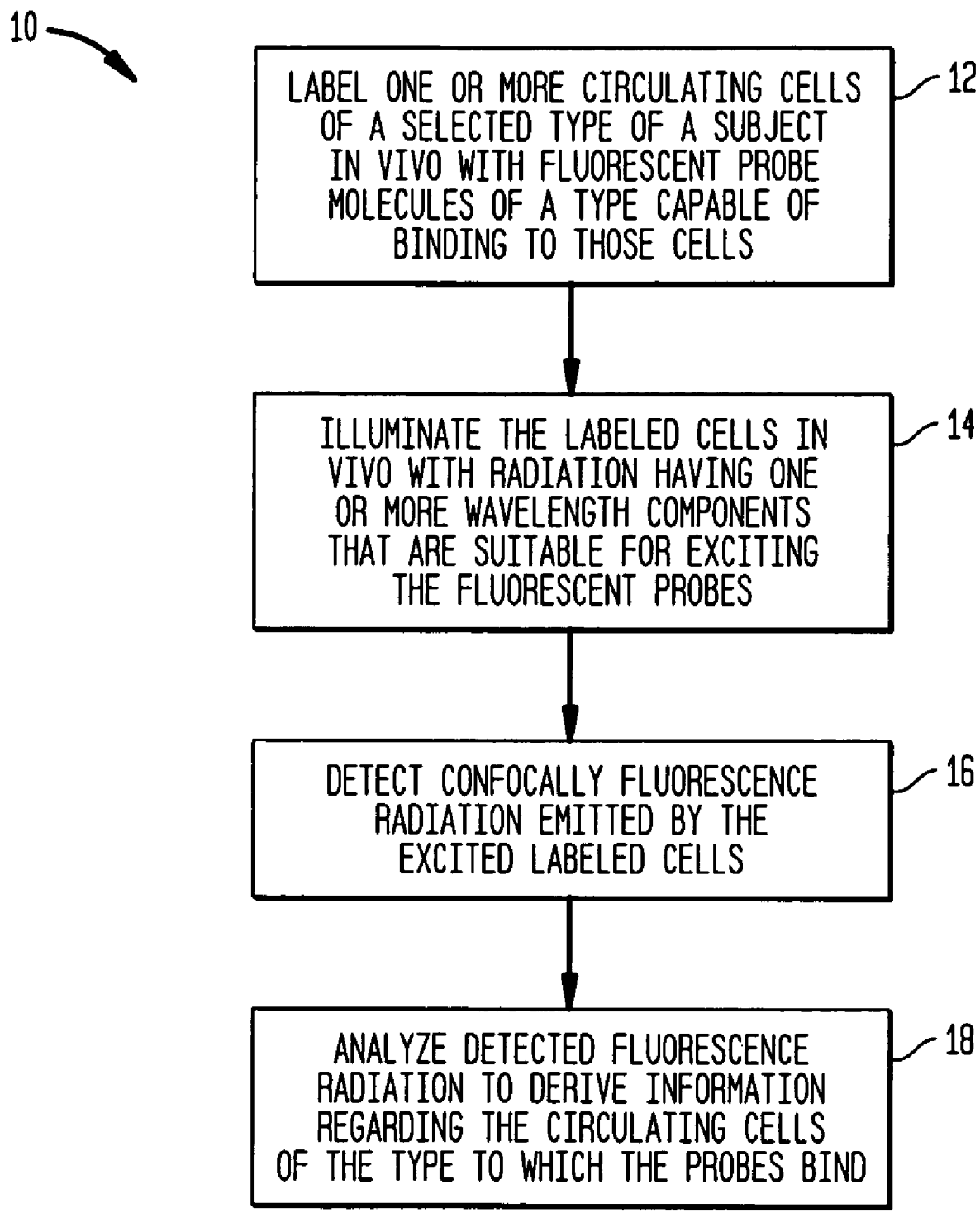
FIG. 1 is a flow chart depicting various steps in one embodiment of a method according to the teachings of the invention for performing in vivo flow cytometry, FIG. 2 schematic illustrates a system according to one embodiment of the invention for performing in vivo flow cytometry, FIG. 3A schematically illustrates a substantially circular cross-section of a radiation beam generated by a radiation source utilized in the system of FIG. 2, FIG. 3B schematically illustrates an elongated radiation beam cross-section, employed for exciting labeled cells passing through a subject's vessel, that is obtained in the system of FIG. 2 by passing radiation from a source having a circular cross-section through a cylindrical lens, FIG. 4 schematically depicts one embodiment of an analysis module that can be utilized in the system of FIG. 2, FIG. 5 schematically depicts another embodiment of an analysis module that can be utilized in the system of FIG. 2.

With reference to a flow chart 10 of FIG. 1, in one exemplary embodiment of a method according to the teachings of invention for performing in vivo cytometry, in an initial step 12, one or more circulating cells of a selected type of a subject, e.g., a patient, are labeled in vivo with fluorescent probe molecules of a type that are capable of binding to those cells. In other words, the cells are labeled while circulating through the subject, i.e., without extraction, ex-vivo labeling and re-introduction of the cells back into the subject. For example, the probe molecules can be injected into the subject's circulatory system to bind to these cells, which also circulate though the subject.

The probe molecules can, for example, couple to one or more surface proteins, e.g., membrane proteins, of the selected cells. In some embodiments, a fluorescent probe molecule can be a fluorescent-labeled anti-body that is capable of binding to a surface antigen of a cell type of interest. Such cell types can include, without limitation, leukocytes, tumor cells, and stem cells. Some examples of suitable antibodies include, without limitation, anti-CD4 for lymphocytes, and PSMA for prostate cancel cells.

Referring again to the flow chart 10, in step 14, the labeled cells are illuminated in vivo, i.e., while circulating through the subject, with radiation having one or more wavelength components that are suitable for exciting the fluorescent probes. In general, the probes are chosen such that they can be activated by radiation that can substantially penetrate through the subject's tissue and blood to reach them. In some embodiments, radiation suitable for activating the probes can have wavelength components in the infrared range of the electromagnetic spectrum. For example, radiation with wavelengths in a range of about 400 nm to about 1000 nm, and more preferably in a range of about 400 nm to about 800 nm, can be employed for exciting the probes. Although many different radiation sources can be utilized in the practice of the invention, in many embodiments, a laser source, such as, a He—Ne laser, generates radiation suitable for activating the probes. Further, in many embodiments of the invention, such as the embodiments discussed below, the radiation source generates a beam that is focused, e.g., by a series of lenses, onto a selected portion of a vessel of the subject.

Upon excitation, the labeled cells, and more particularly their attached fluorescent probe molecules, emit fluorescence radiation, which is typically red-shifted (i.e., it has a higher wavelength) relative to the excitation radiation. In a step 16, this fluorescence emission is confocally detected. The term "confocal detection" is known in the art, and to the extent that any further explanation is required, it refers to detecting the fluorescence photons in a plane that is conjugate to a plane of the excitation radiation that is focused onto a selected portion of a subject's circulatory system, e.g., a vessel, to excite the probe molecules flowing therethrough.

In step 18, the detected fluorescence can be analyzed so as to derive information regarding the circulating cells of the type to which the probes bind. Such information can include, without limitation, the concentration of such cells in the subject's circulatory system, their average flow velocity, size and circulation lifetime. For example, in some embodiments, the fluorescence radiation can be analyzed to obtain a cell count of a particular cell type relative to a previously-measured cell count (e.g., by utilizing relative number of fluorescent peaks counted in a selected time interval). By way of example, such a relative cell count measurement can provide a medical practitioner with information regarding presence and/or progression of a disease and/or efficacy of a previously-applied treatment. For example, the above method of invention can be utilized to derive a relative cell count of tumor cells of a particular type circulating through a patient's circulatory system, thereby allowing assessment of the effectiveness of a treatment protocol.

In some embodiments, the detected fluorescence can be employed to determine an absolute cell count of the cell type of interest. The number of target cells of interest in a given probe volume of blood, at a give time, flowing through a vessel can be given by the following relation:

$$n=[C]*A*v*\Delta t$$

where [C] denotes the concentration of cells to be analyzed (e.g., number of cells/ml), A denotes the cross-sectional area of the vessel, v is an average flow velocity of blood through the vessel, and $\Delta t$ is the sampling time. The product $A*v*\Delta t$ denotes the probe volume. Parameter n is the measured cell number for a given measurement period $\Delta t$. Therefore, if A and v are known, then [C] can be determined. In many embodiments, vessel diameters in a range of about 30 to about 100 microns are employed for cell counting. Larger vessel can also be employed, e.g., for detecting tumor cells.

In an alternative embodiment, the labeling of the cells of interest with fluorescent probes is performed ex vivo, that is, after extraction of the cells from a subject. The labeled cells are then re-introduced into the subject's circulatory system, and are irradiated so as to excite the probes. The fluorescence radiation emitted by the excited probes is detected and analyzed to derive the desired cytometric information. Alternatively, fluorescent proteins can be expressed in a selected cell type of a subject, for example, by employing reporter genes (e.g., GFP).

Figure 2:
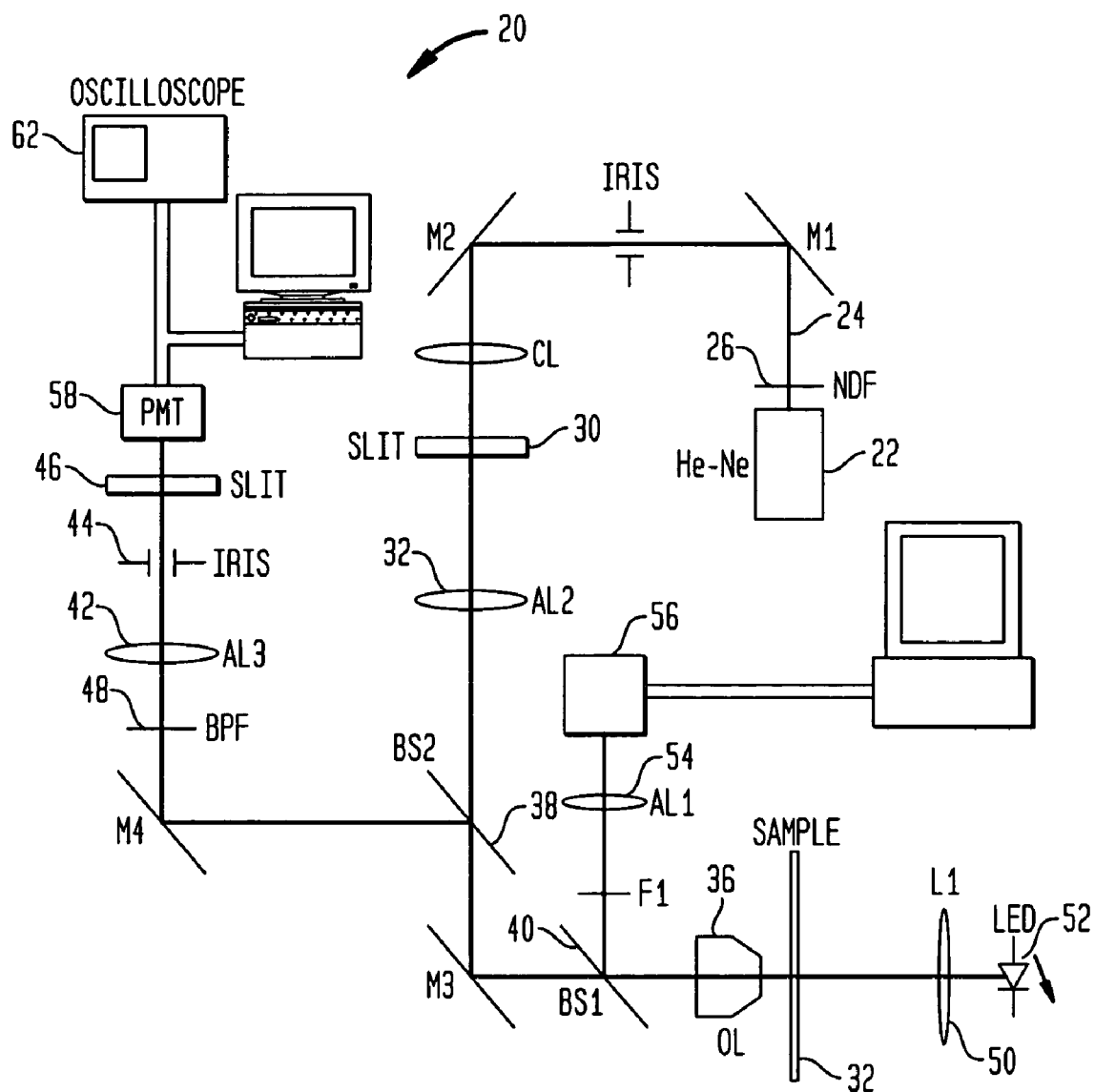

FIG. 2 schematically illustrates a system 20 according to one exemplary embodiment of the invention for performing in vivo flow cytometry in accordance with the teachings of the invention, for example, a system by which the above described method of in vivo flow cytometry can be practiced. The exemplary system 20 includes a radiation source 22 for generating a beam of photons 24 suitable for exciting probe molecules previously administered to a subject under examination. In this embodiment, the radiation source is a He—Ne laser that generates a continuous-wave (CW) lasing radiation at a wavelength of 633 nm. Without any limitation, in this embodiment, the He—Ne laser generates a laser beam having a substantially circular cross-section in a plane perpendicular to the propagation direction and a substantially Gaussian intensity profile in that plane. Those having ordinary skill in the art will appreciate the radiation beams having different cross-sectional shapes and/or cross-sectional intensity profiles can also be utilized.

Figure 3A:
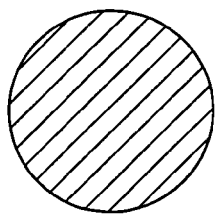
Figure 3B:

The radiation generated by the He—Ne laser passes through a neutral density filter (NDF) 26 that can adjust the radiation intensity to a desired level. Typically, a radiation intensity in a range of about 0.5 to about 5000 W/cm$^2$, and more preferably in a range of about 5 to about 500 W/cm$^2$ is employed. A mirror M1 directs the radiation received from the NDF 26, through an optional iris 28 for filtering out stray light, to another mirror M2 that in turn reflects the radiation towards a cylindrical lens CL. The cylindrical lens CL exhibits different magnifications along two orthogonal axes forming a plane perpendicular to the beam's propagating direction. Hence, it changes the circular cross-section of the beam 24, shown schematically in FIG. 3A, to one having an elongated shape characterized by substantially perpendicular long and short axes, shown schematically in FIG. 3B. Further, the cylindrical lens directs the radiation beam onto a slit 30 that in turn images, via an optical system described below, onto a portion of a selected vessel of the subject positioned in a plane 32, herein also referred to as a sample plane. The vessel of interest is preferably positioned such that the long dimension of the slit traverses the width of the blood vessel. In this manner, circulating labeled cells are excited as they pass through the image of the slit traversing the vessel, as discussed in more detail below. In some embodiments, a mounting mechanism (not shown here) can be utilized to fixate the vessel portion in the sample plane.

Referring again to FIG. 2, an achromatic convergent lens 34 directs the radiation received from the slit 30 to a microscope objective lens 36 that in turn images the radiation onto a portion of a vessel of interest. More specifically, the radiation refracted by lens 34 passes through a dichroic beam splitter 38 to be directed by a mirror M3 through another dichroic beam splitter 40 to the objective lens 36. In this embodiment, the objective lens exhibits a magnification of 40× and a numerical aperture of about 0.6. Those having ordinary skill in the art will appreciate that lenses that exhibit different magnifications and/or numerical apertures can also be utilized. The size of the slit's image on the image plane of the objective lens, i.e., the sample plane 32, and the depth of focus of the image (i.e., the full width at half maximum (FWHM) of the slit image in the axial direction (direction of light propagation)) can be chosen, for example, based on the type of a vessel of interest and the size of the vessel's portion to be illuminated. For example, in this embodiment, the slit's image can have a size of approximately 5 microns by 72 microns with a depth of focus of about 50 microns.

The exemplary in vivo flow cytometry system 20 also includes an optical subsystem for identifying a blood vessel suitable for use in cytometric measurements performed in accordance with the teachings of the invention. More specifically, a lens 50 focuses radiation from a source 52, such as a light emitting diode (LED), onto the image plane 32 to transluminate, or epi-illuminate, a portion of a subject's tissue, e.g., a portion of the subject's finger or ear, that is positioned in the image plane and can contain a suitable vessel. The subject's tissue portion can be fixated in the image plane via a mount or other suitable mechanisms known to those having ordinary skill in the art. In this embodiment, a green LED generating radiation at a wavelength of 520 nm is utilized to provide a good contrast for blood vessels due to hemoglobin absorption. The objective lens 36 directs the transmitted radiation to the dichroic beam splitter 40, which is selected so as to reflect this radiation onto a lens 54 that in turn focuses the radiation onto an image detector 56 for generating an image of the illuminated tissue portion. In this embodiment, the image detector 56 comprises a CCD camera that generates a digital image of the transilluminated portion. The image can be inspected to identify a suitable vessel, for example, a vessel having a diameter in a range of about 20 microns to about 50 microns. While the upper size limit may be determined by the depth of focus provided by the excitation optics, in general, capillary vessels smaller than about 20 microns are not utilized because tumor cells and some white cells may not be able to pass through them freely. Moreover, capillary cells yield count rates that can be too low for most cells of interest.

In many embodiments, the dichroic beam splitter 40 reflects a fraction (e.g., about 1%) of backscattered excitation radiation (e.g., in this embodiment, a portion of He—Ne radiation backscattered from the sample plane) onto the imager 56, thus facilitating alignment of the image of the excitation slit 40 onto a selected blood vessel positioned in the sample plane 32. A precise determination of a measurement location can allow obtaining repeated measurements from the same location over a selected time period, thereby enhancing measurement accuracy in temporal studies.

With continued reference to FIG. 2, fluorescence radiation emitted by the labeled cells, subsequent to their excitation as they flow through the illuminated portion of the selected vessel, is imaged by the objective lens 36 and an achromatic convergent lens 42, through an iris 44, onto a detection slit 46. More specifically, the objective lens 36 directs the emitted fluorescence radiation through the dichroic beam splitter 40, and via the mirror M3, onto the dichroic beam splitter 38. The beam splitter 38 is selected so as to allow passage of the excitation radiation while reflecting the fluorescence radiation towards a mirror M4, which in turn reflects the radiation towards the lens 42 through a band pass filter (BPF) 48. The filter 48 preferably exhibits a high transmission coefficient (essentially 100%) for a range of wavelengths associated with the fluorescence radiation and a substantially lower transmission coefficient for wavelengths beyond this range so as to block interfering radiation, e.g., scattered radiation. For example, in this embodiment, the BPF 48 exhibits a transmission range of about 670 nm to about 720 nm to prevent most of the backscattered excitation light from entering a detector 58.

In this exemplary embodiment, the detection slit 46 is confocally positioned relative to the excitation slit 30. That is, the detection slit is located in an optically conjugate plane relative to the excitation slit. In other words, only those photons, such as fluorescence photons, that originate from the image plane of the excitation slit are substantially imaged onto the detection slit. This allows efficiently detecting fluorescence radiation emitted from a selected excitation volume while minimizing detection of interfering photons that originate from regions beyond this volume. In particular, even if such interfering photons reach the detection plane, they will not be generally in focus in that plane. In other words, the confocal arrangement substantially eliminates detection of radiation from out-of-focus fluorescent and/or scattering sources.

The size of the detection slit can also be chosen to maximize detection of the fluorescent signals while minimizing detection of interfering photons. Although in this embodiment, the detection slit has a size of about 200 microns by 3000 microns, those having ordinary skill in the art will appreciate that other sizes can also be employed. The detector 58, which is placed directly behind the detection slit 46, detects the emitted fluorescence radiation, and transmits the detected signals to an analysis module 60, such as a computer on which software for analysis of the data in accordance with the teachings of the invention is stored. In this embodiment, the output of the fluorescence detector is also transmitted to an oscilloscope 62 that allows observing in real-time the detected flurorescent traces.

In this exemplary embodiment, the fluorescence detector 58 is a photomultiplier tube (PMT), equipped with a data acquisition card, that samples the received fluorescence radiation at a rate of about 100 kHz to generate digitized fluorescence signals for transmission to the analysis module 60. In other embodiments, the detector can be an avalanche photodiode (APD) or any other suitable detector known to those having ordinary skill in the art.

Figure 4:
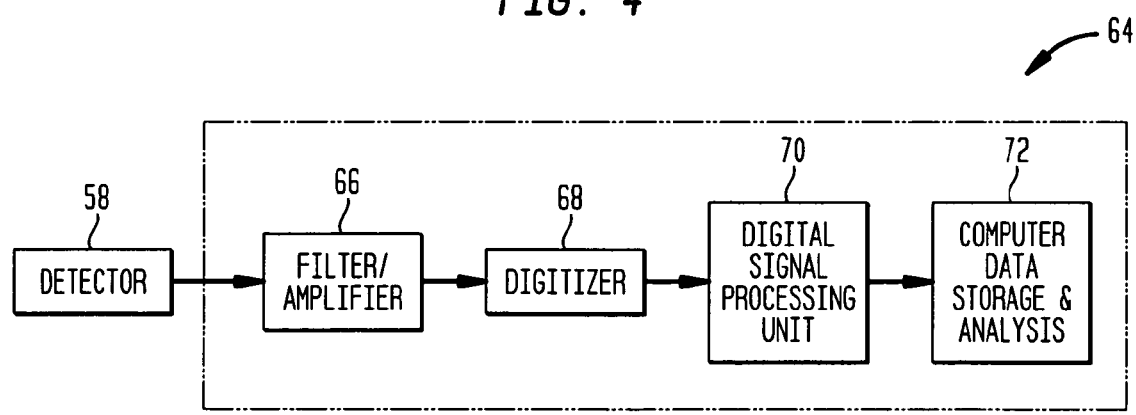

FIG. 4 schematically illustrates some components of an exemplary analysis module 64 suitable for use in the practice of the invention. The exemplary module 64 includes a filter/amplifier 66 that receives the detector's output signal and operates on that signal to remove excess noise, e.g., high frequency noise, and amplifies the signal. Because each labeled cell that moves through the excitation volume gives rise to fluorescence emission pulse whose width has a characteristic frequency consistent with the blood flow, noise components outside this range are preferably removed to improve the signal-to-noise ratio. By way of example, the filter can be a low pass filter with a cut-off frequency less than about 5 kHz that operates on the data to substantially remove high frequency noise, e.g., noise having frequencies higher than about 5 kHz. Further, a threshold filter can be employed to reject fluorescence signals having amplitudes below a selected value. In many embodiments, control measurements can be performed at the data acquisition location before any fluorescent labels are introduced into the subject's blood stream to determine the noise statistics in order to set a noise level above which detected fluorescent peaks will be counted, and below which the signals will be considered as noise. For example, only those fluorescence peaks whose heights are more than about 2 times higher (or more than about 4 times higher) than root-mean-square (rms) of the measured noise can be accepted.

With continued reference to FIG. 4, the exemplary analysis module 64 further includes a digitizer 68 that converts an analog signal received from the filter/amplifier 66 to a digital signal. In this exemplary embodiment, the sampling rate of the digitizer is in a range of about 1 to about 100 kilohertz. A digital signal processing unit (DSP) 70 performs digital noise filtering on the digital signal provided by the digitizer to further enhance the signal-to-noise ratio. The DSP can also be programmed in a manner known in the art to perform peak identification and peak counting. The exemplary analysis module 64 further includes a computer data storage and analysis unit that is employed for storing the digitized fluorescence data and to process the data to derive selected information about cell types of interest in a manner discussed in more detail below. Although the depicted analysis module 64 includes one detection and analysis channel, it should be understood that in other embodiments multiple channels can be employed to detect and analyzed data regarding multiple cell labels (e.g., at different wavelengths).

Figure 5:
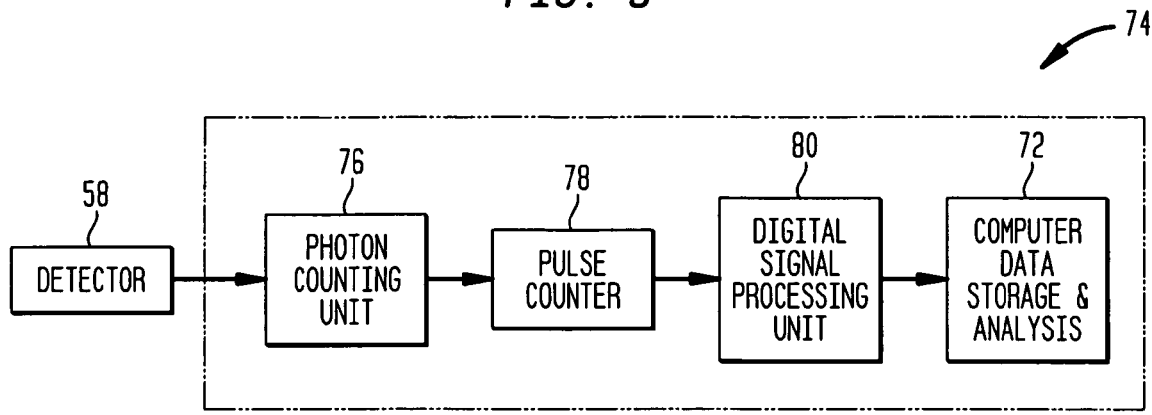

FIG. 5 schematically illustrates an alternative analysis module 74 suitable for use in an in vivo flow cytometry system of the invention, such as that described above, that includes a photon-counting unit 76 for converting individual photoelectric pulses generated by the detector 58, e.g., a PMT or an APD, to TTL logic pulses after performing appropriate pulse height discrimination to reject noise peaks. A pulse counter 78 whose gate widths are set to record photon bursts emitted by cells flowing through the excitation (probe) volume (the gate widths are typically are set in a range of about 10 microseconds to about 10 milliseconds) counts the TTL pulses. A DSP 80 is optionally utilized to operate on the output of the pulse counter for signal-to-noise enhancement and peak identification. A computer data storage and analysis unit 72 stores the output data of the DSP and provides analysis of data in accord with the teachings of the invention.

For each accepted intensity peak, a peak width can be determined. In many embodiments of the invention, a peak width is defined as full width at half maximum (FWHM) of the peak's intensity profile. Those having ordinary skill in the art will appreciate that alternative measures of a peak's width, such as, half width at half maximum, can also be utilized. Those intensity peaks having widths that comply with a defined criterion can be retained while those that do not can be rejected. For example, one or more peaks having widths that are much smaller than what would be reasonably expected for a bona fide fluorescent signal emitted by an excited labeled cell can be discarded. For example, when detecting fluorescence from cells circulating in an arterial vessel, the signal width is expected typically to be larger than about 0.1 millisecond. Hence, signals having smaller widths can be considered as spurious.

Hence, a data set containing accepted fluorescent intensity peaks and their associated detection times, e.g., each relative to the beginning of a measurement period, can be compiled. This data set can be plotted, if desired, as a signal trace indicating fluorescence signal intensity as a function of time. FIGS. 4 and 5, discussed in more detail below in connection with Example 1, illustrate such exemplary signal traces 82 and 84, respectively. The intensity peaks within a measurement period can be counted to provide a cell count during that period. In many embodiments of the invention, a one-to-one relationship is assumed between a fluorescence peak and a labeled cell. In other words, each peak is presumed to be generated by a single labeled cell, rather than a cell cluster. Such a cell count can be compared with a previously measured cell count, obtained via methods such as those described herein or otherwise, to generate a relative cell count. Such a relative cell count can be useful in a variety of applications. For example, a relative cell count of selected tumor cells can provide an indication of efficacy of a particular treatment and/or progression of the disease. By way of example, a high white blood cell count can indicate infection and/or inflammation. Moreover, stem cell counts can be employed in tissue regeneration applications.

Further, the fluorescent signal widths can be employed to obtain information regarding the flow velocity of the labeled cells, and more generally about the flow velocity of cells of that type. In general, the fluorescent lifetime of the excited probe molecules is much shorter than the transit time of a labeled cell through the illuminated portion of a vessel in which the cell travels (a typical fluorescent lifetime can be in a range of about 1 nanosecond to about 10 nanoseconds whereas a typical transit time in a small artery can be in a range of about 1 to about 10 milliseconds). Hence, the width of a fluorescent signal emitted by an excited labeled cell as it traverses the image of the illuminating slit 30 is related to that cell's transit time. In some embodiments, the distribution of the widths of fluorescent peaks can be plotted as a histogram from which a flow velocity can be extracted.

Further, variations of fluorescent signal peaks can be utilized to obtain a statistical measure, e.g., standard deviation, of the uncertainty in the calculated flow velocity. By way of example, exemplary variations among a plurality of measured widths of fluorescent peaks in a data set obtained in accordance with the methods of the invention is shown as histogram in FIG. 8.

Figure 8:
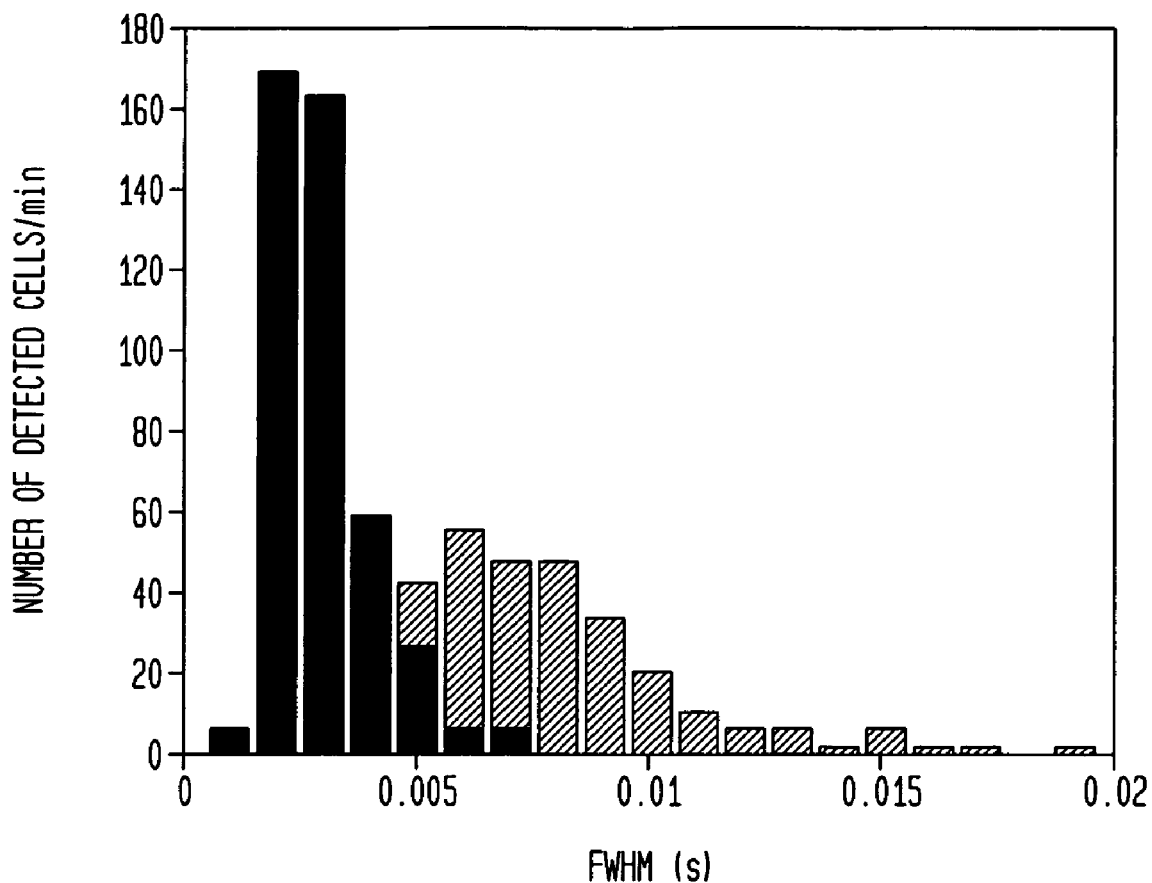
FIG. 8 is a histogram representing the number of fluorescence peaks observed per minute with a specific width (FWHM) associated with radiation emitted by excited DiD-labeled red blood cells flowing in an artery (solid black) and through a vein (gray) of a mouse ear, FIG. 9 schematically illustrates an observed fluorescence peak that can be interpreted as a single peak or as two separate peaks based on algorithms according to the teachings of the invention.
Figure 9:
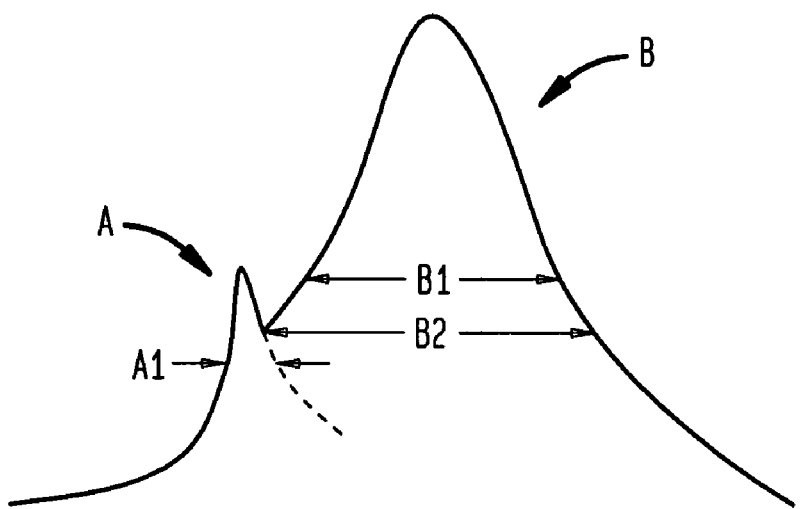

In some cases, two or more apparent fluorescence peaks can be partially overlapping, thereby requiring criteria for determining whether they should be counted as a single peak or multiple peaks. In some embodiments of the invention, the widths of such overlapping peaks are considered in deciding whether they constitute a single peak or multiple peaks. By way of example, FIG. 8 schematically illustrates two apparent partially overlapping peaks A and B. Initially, widths A1 and B1, each corresponding to full width as half maximum, are assigned to these peaks. Assuming that B1 is sufficiently broad to be above a pre-defined threshold (such as that described above), if A1 is smaller than such a threshold, the two peaks are considered as a single peak having a width B2, which is somewhat larger than the initially assigned width B1. Otherwise, if similar to B2, A1 is also above the predefined threshold, the two apparent peaks are considered as two separate peaks each having the initially assigned widths A or B.

In another embodiment of the invention, identifying and counting the intensity peaks in a fluorescent signal trace can be achieved as follows. Initially, a selected percentage (and possibly all) of detected signals points in a trace (i.e., signal intensity as a function of time) are utilized to determine an average and a standard deviation for the background signal (i.e., noise level). For example, data points in one or more signal traces obtained without excitation (and hence without fluorescence peaks) can be employed for this purpose. A threshold level above which data points are assumed to belong to a fluorescent peak can then be set based on the average and the standard deviation of the noise level (e.g., the threshold can be one or more standard deviations above the average). The data points in trace are then examined to determine whether they lie below or above threshold. In this manner, one or more fluorescent peaks, if any, and their associated time can be identified in the data trace. For each peak, intervals to the left and the right of the peak within which the signal intensity falls back to background levels (e.g., falls below the threshold) are determined. In addition, the full width at half maximum (FWHM) of each identified peak is determined by recording the signal points on either side of the peak at which the peak's intensity drops to one half of its maximum value.

In this alternative embodiment, the following algorithm is employed to determine whether two closely-spaced peaks will be counted as a single peak or multiple peaks. The minimum signal intensity between the two peaks, as well as its time index (i.e., time stamp), are identified. If the two peaks comprise third or higher peaks in a trace, the minimum signal intensity and the associated time stamp for two previous peaks are also determined. If the minimum signal intensity between the peak under examination and previous peak(s) is at background noise level (e.g., it is below the selected threshold), then the peak is counted. If the minimum signal intensity (or intensities) between the peak under examination and the previous peak(s) is above the background noise level, the peak will nonetheless be counted (the peak and the previous peak are counted as two separate peaks) if the intensity of both peaks and the minimum signal intensity between them satisfy certain criteria (e.g., when the minimum signal intensity is less than a pre-set fraction of peak heights) Otherwise, if one of the two peaks under examination is high intensity peak (i.e., its intensity is above a selected value), and the minimum signal intensity between the two peaks under examination is above the background level but the minimum signal intensity between two previous peaks is below the background level, only the higher intensity peak will be counted. If neither of two peaks constitutes a high intensity peak and the minimum signal intensity between them is above the expected background noise level, then only one of the peaks, and more specifically the peak having the higher intensity, will be counted.

The Example below provides further understanding of salient features of one embodiment of a method according to the teachings of the invention for performing in vivo flow cytometry.

Example

A number of measurements were performed in mice to demonstrate the efficacy of the methods and systems according to the teachings of the invention for real-time in vivo quantification of circulating cells in a subject. For these measurements, human red blood cells (RBC) were isolated and labeled ex vivo with 0.1 mM DiD (Molecular Probe V22887) (a lipophilic dye that binds to cell membranes). The labeled cells were then injected into a mouse's circulation through the tail vein. In these illustrative measurements, an ex vivo labeling procedure, rather than direct injection into the mouse's circulatory system, was employed so as to limit the fraction of labeled RBC's to less than about 1% in order to avoid overlap of signal pulses.

An instrument such as the above system 20 was employed to acquire the fluorescent data. More specifically, a He—Ne light source was employed for generating excitation radiation. To identify a blood vessel location for measurement, the mouse's ear was transluminated by light from a green LED, and the transmitted light was detected by a CCD to generate an image of the illuminated portion. A fraction of the He—Ne light reflected onto the CCD, together with the transluminated image, were then employed to align the excitation slit on a blood vessel of interest.

Figure 6:
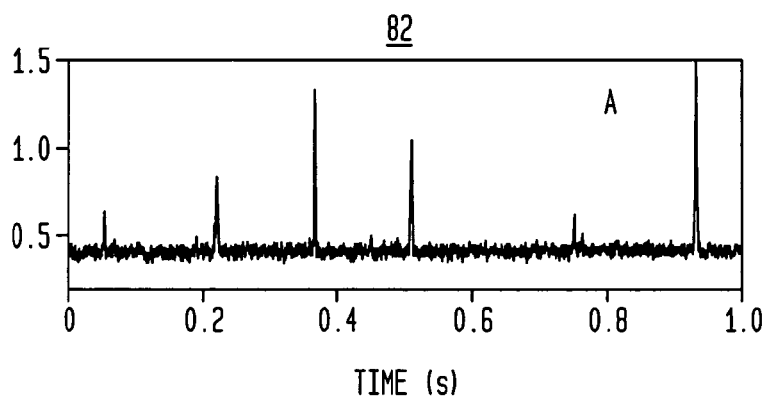
FIG. 6 is a fluorescence trace obtained from labeled human red blood cells flowing through an artery by utilizing a system according to the teachings of the invention.
Figure 7:
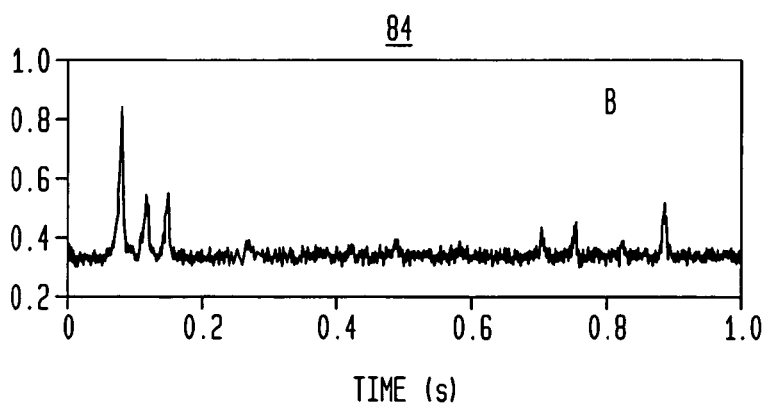
FIG. 7 is a fluorescence trace obtained from human red blood cells flowing through a vein by utilizing a system according to the teachings of the invention.

FIGS. 6 and 7 present typical fluorescence data traces acquired from the mouse ear vasculature. The peaks correspond to fluorescence emitted by the labeled red blood cells. While trace 82 (FIG. 6) illustrates data acquired from an artery, trace 84 (FIG. 7) illustrates data acquired from a vein. Obtaining fluorescence data from an artery as well as a corresponding vein allows assessing the instrument's capability for detecting differences in flow characteristics between arteries and veins. The variations in peak heights can be attributed to several factors, including differences in orientation and the vessel depth of different (nonspherical) RBC's as they pass through an illuminated portion of the vessel, as well as cell-to-cell variability in staining intensity.

FIG. 8 provides pulse width distribution data for fluorescence peaks corresponding to labeled cells detected in the two types of vessels. The pulse width data can be utilized in a manner described above to derive a flow velocity of about 3 mm/second for the artery and a flow velocity of about 1 mm/second for the vein.

Figure 10:
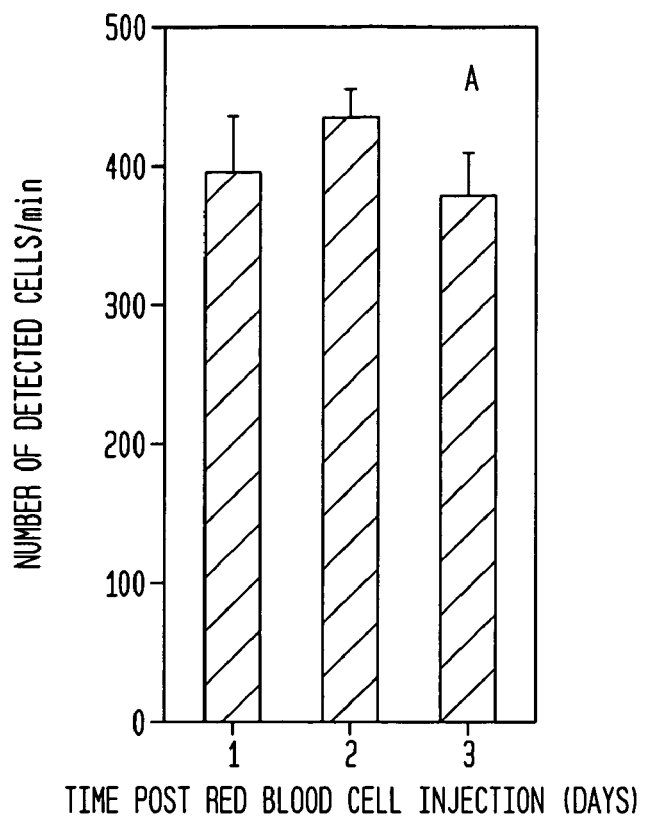
FIG. 10 is a graph illustrating a number of human red blood cells labeled ex vivo and injected in a mouse's circulatory system through the tail vein, as function of days elapsed since the injection.

To quantify the number of fluorescently labeled circulating cells in a reproducible manner, fluorescent measurements were recorded over a 3 day period from the same artery of a mouse injected with DiD-labeled human RBC's, as described above. The mean and standard deviation of the number of cells per minute passing through the selected artery on a given day was calculated from three traces, each of which was 2 minutes in duration. As shown in FIG. 10, variations in the average number of cells per minute passing through the artery among the three observation days were relatively small.

Figure 11:
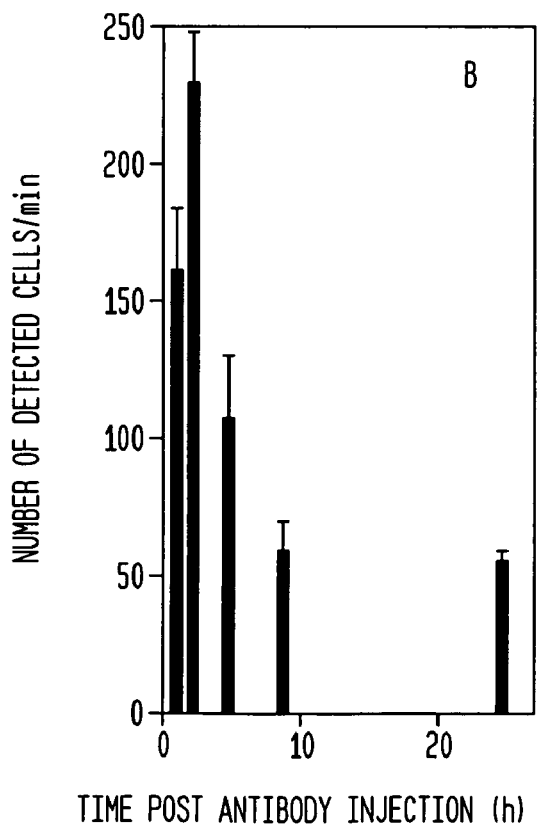
FIG. 11 is a graph illustrating a number of white blood cells, labeled in vivo with a fluorescently tagged antibody as a function of hours elapsed since the introduction of fluorescent tags into blood.

In another series of experiments, a mouse white blood cells (WBCs) were labeled in vivo with a fluorescently tagged antibody. More specifically, 20 micrograms of rat antimouse CD45 monoclonal antibody labeled with Cy-Chrome was injected through the tail vein of a 6-8 week old BALB/c mouse, which was anesthetized with a mixture of ketamine and xylazine (7:1 ratio). In vivo flow cytometry measurements were performed, in a manner similar to those described above, at 0.4, 1.4, 4.3, 8.3 and 25 hour intervals after the injections of the labeled antibody. Upon introduction into the mouse vasculature, the antibody labels the circulating white blood cells that express the CD45 antigen on their surface. The increase in the number of fluorescently labeled WBCs detected within the first 1.4 hour of injection represents the kinetic of antibody binding. The number then decreases rapidly by approximately 75% within the first 8 hours. Such a decrease is understandable because the circulation time of some WBC populations, such as neutrophils, is of the order of hours. In addition, WBCs can be eliminated by either lysis or phagocytosis as a result of antibody binding. Such variations can be observed in FIG. 11, which illustrates that the number of fluorescently tagged WBCs varies dynamically as a function of time relative to the time of the injection of the fluorescently labeled antibody.

In another aspect, the methods and systems of the invention for performing in-vivo flow cytometry can be employed for non-invasive (e.g., without drawing blood samples) in-vivo detection of dying or dead cells (non-viable cells) present in a subject's circulatory system. Some examples of such non-viable cells include, without limitation, apoptotic tumor cells and apoptotic endothelial cells. Such detection of apoptotic tumor cells in a patient's circulatory system can be useful, e.g., for in-vivo monitoring of anti-tumor therapies. Likewise, the detection of apoptotic endothelial cells can be used for monitoring the progress of anti-angiogenic therapies.

Figure 12:
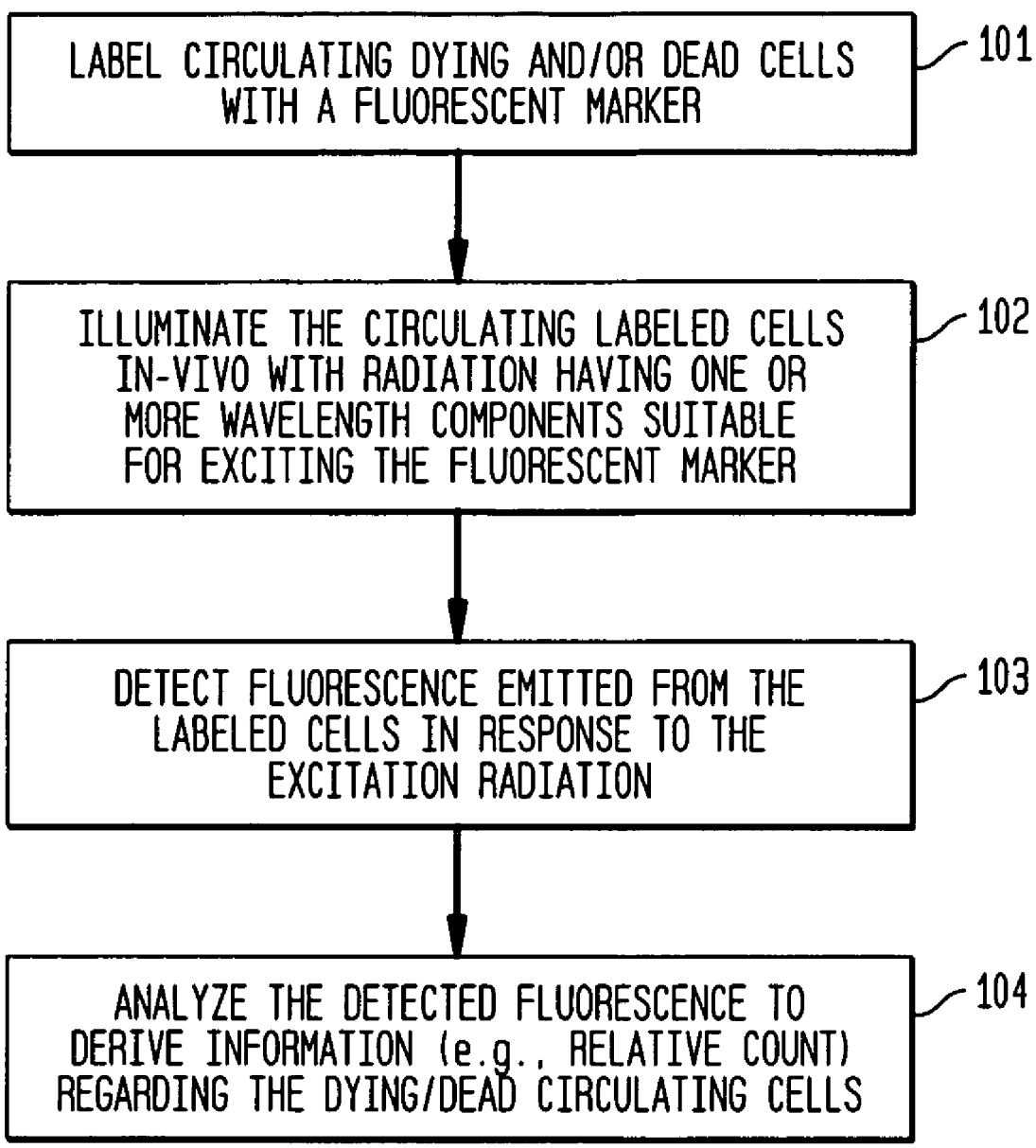
FIG. 12 is a flow chart depicting various steps in a method according to one exemplary embodiment of the invention for in-vivo detection of circulating non-viable cells.

Referring to a flow chart 100 of FIG. 12, in one embodiment, in an initial step 101, a plurality of circulating dying/dead cells (e.g., apoptic cells) in a subject are labeled by a fluorescent marker, e.g., by injecting the subject with a suitable dose. By way of example, a cell marker commonly known as annexin-V conjugated to Alexa Fluor 647 (AF647) can be employed to label exposed phosphatidylserine on the surface of circulating apoptic cells. The long wavelength of AF647 fluorescence, emitted in response to a suitable excitation, allows its detection through blood with minimum attenuation by red blood cells.

Subsequently, in step 102, the labeled cells are illuminated in-vivo, i.e., while circulating through the subject, with radiation having one or more wavelength components that are suitable for exciting the fluorescent markers. As in the previous embodiments, the markers are chosen such that they can be activated by radiation that can substantially penetrate through the subject's tissue and blood to excite them. In some embodiments, radiation suitable for activating the markers can have wavelength components in the infrared range of the electromagnetic spectrum. For example, radiation with wavelengths in a range of about 400 nm to about 1000 nm can be employed for exciting the markers.

In step 103, the fluorescence radiation emitted by the markers is detected, preferably confocally relative to the excitation radiation. The detected fluorescence is then analyzed in a manner discussed above to derive information (e.g., a relative count) regarding the dying/dead cells.

The optical systems and the methods of signal processing described above can be similarly employed to excite the labeled dying/dead cells as well as detect and analyze the emitted fluorescence.

The methods and systems of the invention for in-vivo non-invasive detection of dying or dead cells can find a variety of applications, such as real-time, continuous monitoring of therapies that induce cell death. For example, they can be employed to quantify cell death, thereby providing information about tumor progression, and in particular about the efficacy of anti-tumor and anti-angiogenic treatments.

In general, homeostasis of cell proliferation and cell death plays an essential role in the maintenance of the function of organs and organisms. In cancer, apoptotic processes occur both spontaneously and can also be induced by anti-tumor therapies. Apoptosis is associated with molecular alterations in the cell membrane, condensation of cytoplasmic proteins, and DNA fragmentation. Cell membrane changes comprise loss of phospholipid asymmetry, resulting in the exposure of phosphatidylserine (PS) on the cell surface. Expression of PS allows clearance of the unwanted cells by the phagocytes. During physiological apoptosis, most of the cell death products are effectively removed by macrophages and neighboring cells and can be found in the circulation in small amounts. However, if the recycling system is impaired or overloaded by malignant pathological conditions, cell death products can accumulate in appreciable quantities in the circulation and can become useful targets in diagnosis, prognosis, and monitoring of the disease.

Qualitative and quantitative changes in cancer cell death along with proliferative alterations are important determinants in the pathogenesis and progression of malignant disease and its responsiveness to therapy. In patients with malignant tumors, therapeutic strategies aim at equilibrating the imbalance between proliferation and degeneration. Depending on type and dosage of the chemo-therapeutic drugs, the modality of radio therapy, and the sensitivity of the tissue, cellular damage can result mostly in arrest of the cell cycle and, in response to insufficient repair, in induction of active apoptotic cell death.

The in-vivo detection of circulating apoptotic cells according to the teachings of the invention can be advantageously utilized for assessment of anti-tumor treatments. Further, unlike conventional techniques that require blood drawing, the non-invasive methods of the invention for detecting/counting circulating apoptotic cells can be applied frequently to monitor the progress of an anti-tumor treatment and to predict early response to therapy, without causing discomfort to the patient.

In addition, the methods and systems of the invention for in-vivo detection of dying or dead cells can be employed in assessing progress of anti-angiogenic cancer therapies. These therapies can induce apoptosis in vascular endothelial cells. A portion of such apoptotic endothelial cells slough off the blood vessels and find their way into the circulation. Thus, measurement of such circulating apoptotic endothelial cells or cancer cells can provide valuable information for an early evaluation and prediction of response to the anti-cancer treatment, thereby enhancing the chances of successful treatment. In addition, the methods and systems of the invention for in-vivo detection of circulating dying or dead cells can be particularly useful for studying small animal models of tumors. In particular, unlike conventional methods that require drawing blood and hence may not allow obtaining several measurements from an animal having a limited blood volume, the non-invasive method of the invention can be utilized to perform multiple measurements on a single animal, thereby minimizing the number of animals needed for a study and decreasing measurement artifacts that could arise from variations between different animals.

To demonstrate the efficacy of the teachings of the invention for detecting in-vivo circulatory dying/dead cells and only for illustrative purposes, the results of prototype experiments utilizing the methods of the invention are discussed below. MatLyLu mouse prostate cancer cells pretreated with camptothecin were employed as a positive control. It was verified by conventional flow cytometry that more than about 80% of the camptothecin-treated cells undergo apoptosis (i.e. >80% of the treated cells were FITC-annexin $V^+$ positive and propidium iodide negative). The camptothecin-treated cells were then labeled with the AF647-conjugated annexin-V and injected intravenously into the mouse. The circulating annexin-$V^+$ cells were measured by focusing a He—Ne laser beam having a wavelength of 633 nm through a slit onto an ear vessel (typically a small artery) and confocally detecting the fluorescent bursts (peaks) as individual cells flowed through the probe beam. The emitted fluorescence was detected by a photomultiplier tube and was digitized for analysis. The confocal detection of the emitted fluorescence allowed continuous monitoring over the measurement period of the labeled cells flowing through the vessel.

Figure 13:
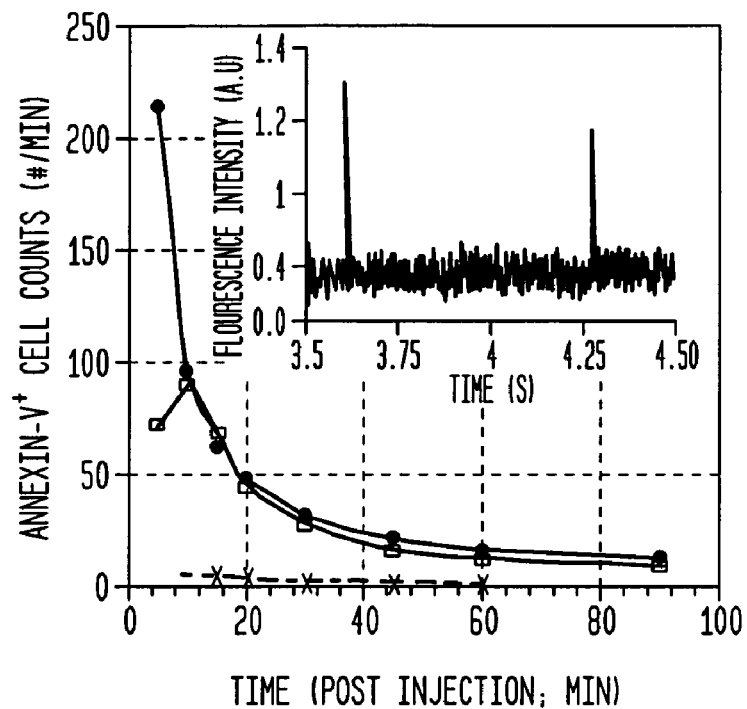
FIG. 13 presents graphs indicating detection of mouse apoptotic cells by employing the teachings of the invention as well as an insert showing fluorescent peaks corresponding to radiation emitted by fluorescently labeled apoptotic cells excited in-vivo by radiation from a He—Ne source.

The insert in FIG. 13 shows such fluorescent bursts. Each peak within the trace indicates the passage of an alexa647-annexin V labeled apoptotic MLL cell through the slit of light that causes excitation of its fluorescent marker, and the emission of a burst of fluorescence by its excited marker. Control measurements were performed at the data acquisition location before introduction of any fluorescent labels into the blood stream to determine a threshold noise level. Only those fluorescent peaks that exceeded that noise level were counted. The number of fluorescent peaks, along with the height and full width at half maximum of each peak, were determined in a manner similar to that described above in connection with the previous embodiments.

As shown by the solid circles in the graph of FIG. 13, the detected cell count dropped from more than about 200/min to less than about 50/min within 20 minutes of injection, indicating rapid clearance.

Subsequently, unlabeled, camptothecin-treated apoptotic MatLyLu cells were introduced into the circulation, followed immediately by injection of the annexin-V probe. As shown by the open squares in one of the graphs in FIG. 13, the cell count increased during the first 5 minutes after the injection due to the in-vivo labeling process. The cells were cleared at same rate as that experienced by in-vitro labeled cells. Control experiments with injection of annexin-V alone yielded negligible cell count, as indicated by the crosses in another graph in FIG. 13.

Figure 14:
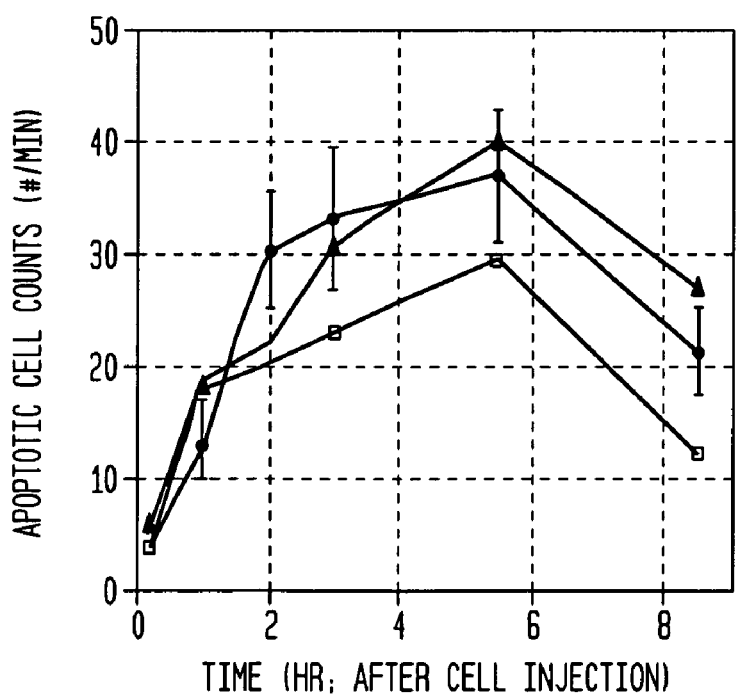
FIG. 14 presents graphs indicating time course of annexin-$V^+$ cell count following the injection of about 1 million untreated MatLyLu cells, 1 million LNCap prostate cancer cells or about 3 million leukemic Nalm-6 cells into a mouse.

When untreated, viable MatLyLu tumor cells were injected into the circulation, no apoptotic cells were initially detected. Circulating annexin-$V^+$ cells were detected starting at one hour after the injection, with the detected cells reaching a plateau at about three hours after the injection, as shown by the solid circles in FIG. 14. Because the total number of circulating MatLyLu cells decreased precipitously during the first three hours, it can be concluded that the fraction of MatLyLu cells undergoing cell death steadily increased during this time. Analysis of extracted blood with standard flow cytometry indicated that about 9% of the injected cells were annexin-$V^+$ at the 3-hour time point.

The above experimental results suggest that MatLyLu cells undergo cell death in circulation within 1-2 hours after injection, possibly due to lack of survival signal from cell adhesion, and the harsh environment imparted by the sheer stress. The studies using LNCaP prostate cancer cells and Nalm-6 leukemic cells gave similar results, as indicated, respectively, by the open squares and solid triangles in FIG. 14.

It should be understood that the above experimental data is provided only for illustrative purposes and to show the efficacy of the teachings of the invention for in-vivo detection of dying/dead circulating cells, and not to necessarily indicate the optimal results (e.g., signal-to-noise) that can be obtained by utilizing the teachings of the invention to count circulating dying/dead cells.

Those having ordinary skill in the art will appreciate that various modifications can be made to the above embodiments of the invention without departing from the scope of the invention. For example, the methods and systems of the invention can be utilized to obtain in vivo flow cytometric data regarding cell types other than those described above and/or employ fluorescence labels other than those discussed above.

What is claimed is:

1. A method for non-invasive detection of non-viable cells in a subject using in-vivo flow cytometry, comprising
    labeling a plurality of non-viable cells circulating in a circulatory system of the subject with one or more fluorescent probe molecules that bind to the non-viable cells while the non-viable cells circulate in the circulatory system of the subject,
    illuminating the labeled cells in-vivo with radiation having one or more wavelength components suitable for exciting said one or more fluorescent probe molecules,
    detecting fluorescence radiation emitted by the labeled cells in response to said excitation, and
    analyzing said detected fluorescence radiation so as to count labeled non-viable circulating cells from which fluorescence is detected.

2. The method of claim 1, wherein said circulating non-viable cells comprise circulating apoptotic cells.

3. The method of claim 2, wherein said apoptotic cells comprise endothelial apoptotic cells.

4. The method of claim 1, wherein said illuminating and detecting steps are performed confocally.

5. The method of claim 1, wherein said count of labeled cells provides a count of said non-viable cells relative to a previously-obtained count of non-viable cells from the subject.

6. The method of claim 1, wherein said illuminating step comprises exposing said labeled cells to radiation having one or more wavelength components in a range of about 400 nm to about 1000 nm.

7. The method of claim 1, wherein said one or more fluorescent robe molecules comprises a molecule suitable for coupling to a cell surface marker of the non-viable cells.

8. The method of claim 7, wherein said one or more fluorescent probe molecules comprises annexin-V conjugated to Alexa Fluor 647.

9. A method for real-time quantification of non-viable circulating cells using in-vivo flow cytometry in a live subject, comprising:
    administering to a circulatory system of the subject a plurality of fluorescent probe molecules capable of coupling to a plurality of non-viable cells,
    illuminating at least a portion of a blood vessel of the subject with radiation capable of exciting said fluorescent probe molecules flowing through said vessel portion,
    confocally detecting fluorescence radiation originating from one or more of said excited probe molecules flowing through said vessel portion, and
    analyzing said detected fluorescence to identify fluorescent signals emitted by probe molecules coupled to said non-viable circulating cells, thereby providing a count of circulating non-viable cells from which fluorescence is detected.

10. The method of claim 9, wherein said analyzing step comprises determining a relative count of said circulating non-viable cells.

11. The method of claim 9, wherein said non-viable cells comprise apoptotic endothelial cells.

* * * * *